United States Patent
Heinz et al.

[11] Patent Number: 5,980,495
[45] Date of Patent: *Nov. 9, 1999

[54] NEEDLE CAP DEVICE FOR A PRE-FILLABLE ONE-TIME INJECTION APPARATUS

[75] Inventors: Jochen Heinz, Vendersheim; Michael Spallek, Ingelheim, both of Germany

[73] Assignee: Claas KGaA, Harsewinkel, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/064,496

[22] Filed: Apr. 22, 1998

[30] Foreign Application Priority Data

Apr. 23, 1997 [DE] Germany .............................. 197 17 033

[51] Int. Cl.$^6$ ................. A61M 5/00; A61M 5/32
[52] U.S. Cl. .................. 604/263; 604/198; 604/199; 128/919
[58] Field of Search ..................... 604/192, 198, 604/199, 263; 128/917, 919

[56] References Cited

U.S. PATENT DOCUMENTS

| | | | |
|---|---|---|---|
| 2,688,963 | 9/1954 | Smith | 604/192 |
| 4,474,734 | 10/1984 | Cooper | 422/34 |
| 4,728,321 | 3/1988 | Chen | 604/110 |
| 4,735,311 | 4/1988 | Lowe et al. | 206/365 |
| 4,986,818 | 1/1991 | Imbert et al. | 604/192 |
| 5,085,647 | 2/1992 | Henderson et al. | 604/192 |
| 5,338,310 | 8/1994 | Lewandowski | 604/192 |

FOREIGN PATENT DOCUMENTS

| | | |
|---|---|---|
| 89 06 101 U | 8/1989 | Germany . |
| 41 40 101 C1 | 7/1993 | Germany . |
| 42 34 319 A1 | 4/1994 | Germany . |
| 0 429 052 B1 | 8/1994 | Germany . |
| 44 38 360 A1 | 5/1996 | Germany . |

*Primary Examiner*—Corrine McDermott
*Assistant Examiner*—Michael J. Hayes
*Attorney, Agent, or Firm*—Michael J. Striker

[57] ABSTRACT

The pre-filled single-use hypodermic devices must be provided with a needle cap device (1) during storage for protection of the injector needle (4) and the contents of the hypodermic device which is removed prior to use. The two-part needle cap device (1) includes a plastic outer casing (5) of hard elastic transparent material which is provided inside with a lining member (6) sealing the tip of the injector needle and made from a soft elastic material. The injector head (2) and the plastic outer casing (5) have a coupling device for making a mechanical stable form-fitting connection and/or a positive-locking connection with a reliable microbiological seal when the injector head (2) is inserted in the outer casing (5). This coupling device is formed by elements on or features of the injector head (2) and outer casing (5). The needle cap according to the invention permits a drop-free removal since the injector head and the form of the needle cap cooperate with and conform to each other so that the tip of the needle injector is released from the lining member (6) only when a pressure inside the outer casing corresponds to the external air pressure.

12 Claims, 4 Drawing Sheets

NEEDLE CAP DEVICE FOR A PRE-FILLABLE ONE-TIME INJECTION APPARATUS

BACKGROUND OF THE INVENTION

The present invention concerns a needle cap device for a pre-fillable one-time injection apparatus with an injector needle firmly connected to an injector head and the resulting improved injection apparatus. This needle cap comprises a stiff plastic outer casing made of a hard elastic material, which is provided with an interior sealing lining member made of a soft elastic material. This needle cap is easily put on the injector head and without any preparatory steps is completely removable from it. The injector head and the stiff plastic outer casing have elements of a mechanically stable form and/or elements providing a force-locking connecting device around the insertion path for the cap, with a microbiologically secure seal when the stiff plastic outer casing is on the injector head.

A pre-filled, one-time injection apparatus, also called a syringe, should be made from glass or plastic, and must be provided during storage with a needle cap, which is removed immediately prior to use, for protection of the injector needle and contents to be injected. The injector needle is also designated a hollow injection needle and the needle cap is designated a protective cap.

This type of needle cap is known and on the market in many different embodiments. Needle caps, which are made from elastomer, preferably synthetic rubber or natural rubber, so-to-say the classical needle cap, are most widely distributed or used. The length of the cap is typically selected so that the tip of the injector needle is inserted in the cap tip when the cap is put on the injector head and remains enclosed and sealed by the material of the cap.

A needle cap of this kind combined with the injector needle firmly connected to the injector head, for example, is known and described by DE-27 17 830 A1 (there by FIG. 6) and DE-44 38 360 A1. Also DE 4 234 319 A1 discloses a needle cap with an elastic cap shroud, which conforms to the injector head. The needle cap of this kind has, on the one hand, the advantageous property that it is easily put on and removed from the injector head without preliminary preparation steps, and also a reliable microbiological seal is guaranteed since the elastic cap shroud conforms to the injector head. However this arrangement has the following disadvantageous properties:

The needle cap can oppose mechanical influences only to a limited extent because of the softness of the material. It can also be penetrated by the needle so that it poses a not insignificant danger of injury to the user.

The needle cap is pressed together when it is removed and contacts on the hollow needle surface. This leads, at least partially, to stripping off of silicone on the needle which serves as a sliding agent for the injection process. If this sliding agent is removed, the injection is associated with pain caused by the injection process. Silicone particles/droplets are thus formed which can enter the body in which the injector needle is inserted.

The assembly of the needle cap is difficult since a reliable controllable displacement limit is absent for the process of placing the needle cap over the injector needle so that the needle cap can easily be pushed too far or too little on the injector head over the needle. Both cases are very disadvantageous since in the first case the needle can poke through the needle cap and in the second case a reliable microbiological seal is no longer guaranteed.

The injector needle is not controllable and/or observable visually by the user with the needle cap placed over the needle on the injector head, to determine, for example, whether the needle is suited for the predetermined purpose or the needle is bent, contaminated or damaged. The needle cap must be removed and if necessary again placed on the injector body with the accompanying great danger of microbiological contamination of the needle, or even of the contents of the needle, and/or of penetration of the needle cap or of needle bending.

During removal of the needle cap a low pressure is produced in the needle tip so that liquid filled in the injector device easily issues from it. It is necessary for the user to remove this liquid drop, which reduces for one thing the actual applied dosage and, for another, the outer needle surface is wetted with medicine. During the injection an indefinite amount of medication is brought into the duct in the needle which is generally undesirable and can lead to bleeding at the insertion location with a few medicines, e.g. anticoagulants (Heparin etc.).

For improvement of the mechanical properties of this type of needle cap it is known to provide the needle cap with an outer hard elastic shell as described in EP 0 429 052. Although needle caps of this type are better protected against mechanical influences and also against penetration by the needle, thus avoiding the above-mentioned injury danger, the other disadvantages—no visual control and no observability of the needle when the needle cap is on the injector head, no drop-free removal of the needle cap, stripping of the needle siliconization and no reliable displacement limit for the cap during assembly.

An additional disadvantage in this embodiment is the limited ability to sterilize the needle with the needle cap covering it: a sterilization with a high energy light flash is not possible, similarly the hard outer jacket prevents a sterilization with steam due to insufficient penetrability of steam through this two-part needle cap.

The alternative needle cap described in the above-mentioned DE 44 38 360 A1 has similar disadvantages. This needle cap includes a plastic outer casing of comparatively hard elastic material which is lined inside with a soft elastic sealing material, at least in the vicinity of the hollow needle point. Because of that this soft elastic material can be selected for optimum sealing properties (sealing function), while the hard elastic material is suitable to counter exterior mechanical damage (protective function).

This known needle cap does not fulfill the following criteria: a) reliable sealing of the tip of the needle, b) visual inspection of the needle with the needle cap placed over it, c) reliable drop-free removal of the needle cap, d) no damage to the siliconization on the needle, e) complete removability of the injector head without preparatory steps, f) sterilizability by light flash, steam sterilization, g) reliable connection of the cap to the injector by definite and controllable positioning and g) reliable resealing of the injector after use.

A needle cap was disclosed with the above-mentioned features in German Utility Model Nr. 89 06 101 which does guarantee a reliable sealing and application of the needle tip. The above-described criteria are however also not fulfilled with this known needle cap.

SUMMARY OF THE INVENTION

It is an object of the present invention to provide a needle cap device of the above-described type which fulfills the above-described criteria and avoids the above-described disadvantages and to provide an improved injection apparatus including this needle cap device.

This object, and others which will be made more apparent hereinafter, is attained in a needle cap device for a prefillable one-time injection apparatus including an injector head, an injector needle firmly connected to the injector head and the needle cap. The needle cap device includes a stiff plastic outer casing made of a comparatively hard elastic material and a sealing lining member made from a comparatively soft material and arranged inside the stiff plastic outer casing at least in the vicinity of a tip of the injector needle when the outer casing is placed on the injector head so that the outer casing is easily placed on the injector head and is easily removed from the injector head without preparatory steps and means for connecting the needle cap to the injector head to provide a mechanically stable connection limiting displacement of the outer casing on the injector head and simultaneously to provide a microbiological seal of an interior of the outer casing from an exterior thereto. The means for connecting the injector head and the stiff plastic outer casing includes elements provided on the injector head and the stiff plastic outer casing.

According to the invention, the stiff plastic outer casing is made of a transparent or semitransparent translucent plastic material, the means for connecting has only one stop position and the injector head and the outer casing are designed to fit each other so that an opening in the tip of the injector needle is released from the lining member in the outer casing during removal of the outer casing from the injector head when a pressure in the interior of the outer casing corresponds to an external air pressure.

The two-part needle cap device according to the invention combines the following advantages:

The transparent needle cap allows a visual inspection of the injector needle by the user even with the needle cap placed over the needle and on the injector head. The damages due to a preliminary withdrawal of the known, non-transparent needle cap—for the purposes of control—are thus avoided. A "control lens" in a two-shell needle cap made of non-transparent material is disclosed in DE 41 40 101 C1 but the needle cap is very expensive to make.

The needle cap of the invention is completely removable from the injector head without preparatory steps, preparatory steps are not required for placing the cap over the needle or taking it off, such preparatory steps including for example rotation, pressing or cutting the needle cap. The deformation of the needle cap does not damage the siliconization of the needle during removal of it.

The form-fitting or positive locking connection (the engagement) of the stiff plastic outer cap with the injector head guarantees a mechanically and microbiologically reliable protection of the outer needle surface and the injector contents. According to another form of the needle cap it can be equipped with an O-ring for sealing of the injector head. The stop integrated in the injector head or in the needle cap limits the displacement of the needle cap relative to the injector head during connection of the two. The engagement of the needle cap on the injector head can be tested to 100% simply and reliably, e.g. by acoustic detection of the noise produced by the connection. A similar connection arrangement is of course also present in the needle cap according to the Utility Model mentioned above. This known needle cap however has connecting elements for two locking connections in two different locking positions along the injector axis, while in contrast the connecting arrangement of the needle cap according to the invention has only one single locking position. Because of that the structure of the needle cap is simpler for one thing and the insertion of the injector head in the cap is uncomplicated for another, because a sensitive fine touch is no longer required in the first locking position as in the known case.

Because of the aeration of the cap interior prior release of the opening in the needle tip from the inner covering lining, a drop-free removal of the needle cap is possible. This is not possible with the known needle cap. An effect on the dosage administered and disadvantageous activity due to wetting of the needle surface are avoided during insertion of the needle through the skin of a patient, a very great advantage for usage of the injector product. The stiff plastic outer cap not only has a mechanical protective function, but allows a displacement-dependent aeration of the cap interior by means of its stable shape, in contrast to the known soft elastic needle caps with which the cap is continuously sealed during removal, cooperating with the injector head and thus preventing aeration of the cap interior.

The replacement of the needle cap after use is made substantially easier when the needle cap and the injector head have a funnel-like conical form.

During replacement of the needle cap after use of the injector a penetration of the needle through the needle cap is reliably prevented first by mechanical guidance of the needle cap and next by the properties of the hard elastic needle casing.

According to a preferred embodiment of the invention, the form-fitting connection between the injector head and the hard plastic outer casing is formed by a snap coupling. This sort of embodiment is comparatively simple to make and guarantees a mechanically very stable and simultaneously reliable seal with very well controllable positioning of the needle cap when the injector head is inserted in the needle cap. According to another embodiment of the invention the snap coupling is advantageously formed so that a groove-like depression in the injector head and a complementary bulged region are formed on the inner wall of the cap.

According to another form of the invention it is also possible to form a snap coupling in such a way that a bulged portion or alternatively a circular collar is provided on the injector head and a complementary groove-like depression is formed in the interior wall of the cap. In both cases the engagement or lock-in noise occurring during connection can be controlled and used as a quality insuring characteristic property.

Various embodiments are available to one skilled in the art in which the features are determined by whether the injector body or the injector head is made from glass or plastic. Plastic injectors may be made with very close tolerances so that in the simplest case a mechanically and microbiologically reliable form-fitting connection it is sufficient to adjust or design the injector head configuration to the configuration of the cap with very narrow tolerances.

In order to aerate the interior of the plastic casing by displacing it during pulling the needle cap off the injector head, a series of possibilities are available to one skilled in the art. Thus according to an additional embodiment of the invention the injector head is formed so that it is conical and tapers to its tip for aeration of the interior of the plastic cap.

According to another form of the invention alternatively the injector head is provided with a longitudinal groove which is released during displacement of the cap for aeration of the interior of the plastic casing. This is possible when the longitudinal groove is V-shaped, widens toward the tip of the injector head and tapers to a point.

The arrangement for displacement-dependent aeration of the interior of the cap can be designed so that the axial position of the form-fitting connection and the axial extent of the inner lining member of the plastic cap are adjusted to each other so that a constrained aeration of the cap interior occurs during removal of the needle cap from the injector head before the needle tip is released from the inner lining member.

BRIEF DESCRIPTION OF THE DRAWING

The objects, features and advantages of the invention will now be illustrated in more detail with the aid of the following description of the preferred embodiments, with reference to the accompanying figures in which.

DESCRIPTION OF THE PREFERRED EMBODIMENTS

Figure 1:
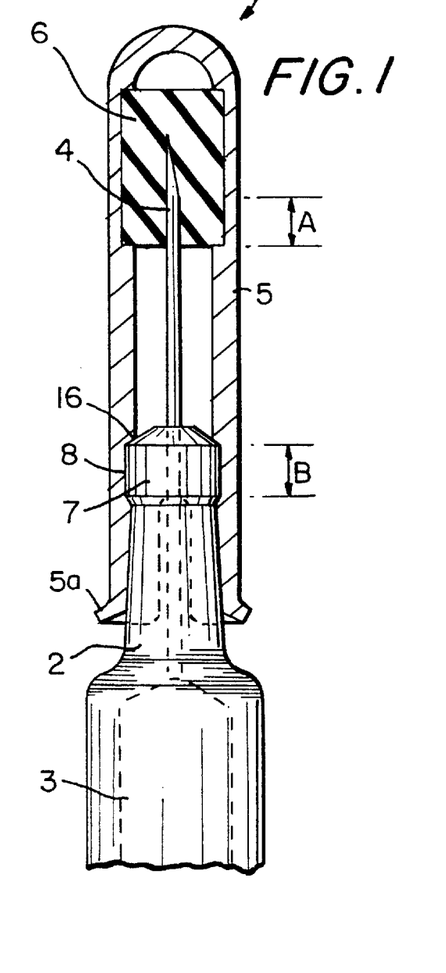
FIG. 1 is a cross-sectional view of a first embodiment of a two-part needle cap device according to the invention with a stiff outer plastic casing closed on all sides.

FIG. 1 shows a general needle cap device indicated with 1 for a pre-fillable one-time injection apparatus with an injection needle 4 firmly connected to the injector head 2 of an injector body 3 of the one-time injection apparatus. The needle cap has two parts, namely an outer plastic casing 5 made from a comparatively hard elastic material (for example transparent polymers such as cycloolefin copolymers (COC), polystyrene, polyethylene terephthalate(PET), polyethylene naphthylate (PEN), polymethylpentene (TP), acrylbutadienestyrene (ABS), polycarbonate (PC) or semi-transparent polymers, such as polyethylene, polypropylene) which is provided with a sealing, lining member made of a comparatively soft material, e.g. natural rubber, halogen butyl elastomer, preferably a translucent rubber-like elastomer (e.g. silicone rubber, thermoplastic elastomer, COC-elastomer). The needle cap has a circumferential guiding conical lip 5a for easy insertion of the injector head in the needle cap. The lining member 6 has a predetermine shape so that it fits in a suitable opening or cavity in the outer plastic casing 5. In another embodiment it is possible to make the outer jacket or casing from the plastic with a soft-elastic thermoplastic elastomer (TPE) or silicone rubber in one process step by means of a two-component injection molding process. The needle tip is sealed by the lining member 6, since the needle is stuck in this part.

The needle cap 1 can be pushed on the needle head 2 and removed from it without preliminary steps. According to a first feature of the invention the plastic cap 5 is made from a transparent plastic material, whereby a visual inspection of the injection needle is possible with the needle cap on the one-time injection apparatus. According to an additional feature of the invention the injector head 2 and the plastic casing 5 have elements of a mechanically stable form-fitting connection device for snap connection. This connection device comprises a circular collar 7 formed on the injector head 2 and a complementary recess 8 provided in the interior wall of the casing. The stop 16 in the cavity 8 provides a controllable limit to the displacement of the needle cap when the injector head 2 is inserted in the needle cap.

According to an additional feature of the invention the injector head 2 and the needle cap 1 are designed to conform to each other so that the opening in the tip of the needle is first released from the soft elastic interior lining member 6 of the plastic cap during removal of the plastic cap when the cap interior is ventilated resulting in a pressure balance, i.e. until the pressure in the cap interior corresponds to the outer air pressure. In the embodiment according to FIG. 1, similarly to the embodiment according to FIGS. 2 to 4, this occurs so that the axial position of the form-fitting connection device 7, 8 and the axial extent of the inner lining member 6 of the plastic casing 5 are predetermined so that the cap interior is aerated in a constrained manner before the opening in the needle tip is released from the inner lining member 6 on removing the needle cap. The drop-free removal is guaranteed because the sealed distance A for the needle point is greater than the sealed distance B of the needle cap on the injector head. Because of that, a drop-free removal of the needle cap is advantageously possible as already mentioned.

In the embodiment according to FIG. 1 the outer plastic casing 5 is closed on all sides. The introduction of the interior soft elastic lining member 6, which advantageously comprises a rubber elastomer, is thus only possible through the associated opening in the outer plastic casing 5 from the injector head side.

Figure 2:
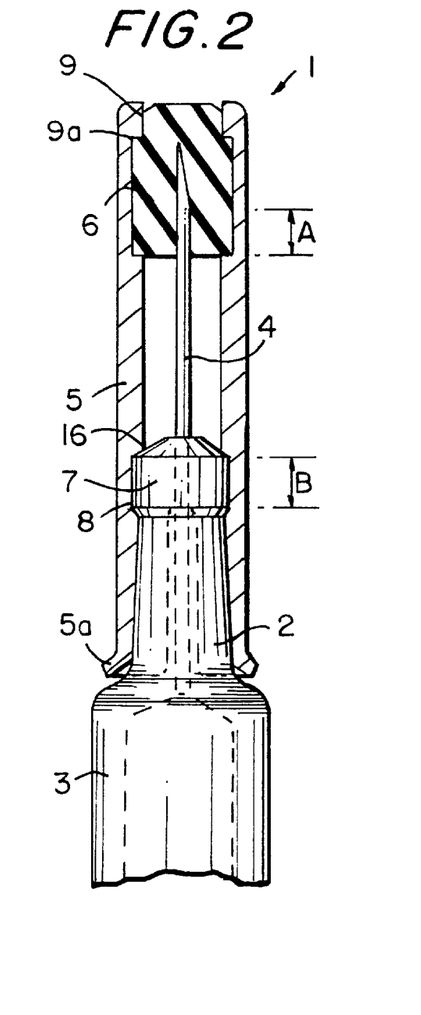
FIG. 2 is a cross-sectional view through another embodiment of a needle cap device according to the invention with a stiff outer plastic casing, which has an opening at its tip which is closable by an interior soft plastic lining member.

In the embodiment according to FIG. 2, which generally conforms to that of FIG. 1, equal parts are provided with the same reference numbers. However the outer plastic casing 5 has an opening 9 in its tip end which is closable by the inner soft elastic lining member 6. In the embodiment according to FIG. 2 inner lining member 6 closes the opening 9 flush with its upper edge. The inner lining member 6 is held on a lower shoulder 9a of the opening. The embodiment according to FIG. 2 permits mounting the inner lining member 6 from the cap tip, which can be more beneficial than the mounting method required for the embodiment of FIG. 1 during manufacturing.

Figure 3:
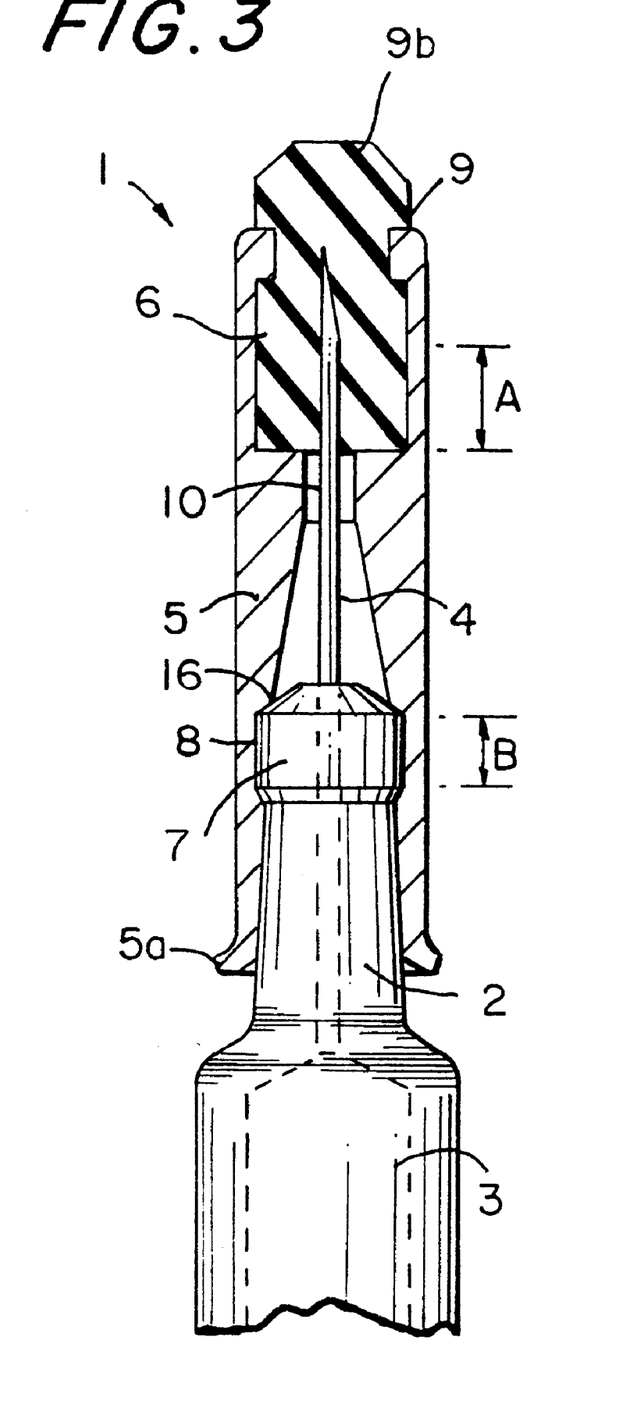
FIG. 3 is a cross-sectional view through a further embodiment of a needle cap device according to the invention with an outer plastic casing, similar to that shown in FIG. 2, which however provides constrained guidance for the injection needle by a reinforced wall.

FIG. 3 shows an additional embodiment similar to that according to FIG. 2 but having the following differences. The inner lining member 6 closing the opening 9 is not flush with its edges, but protrudes somewhat. The inner lining member 6 can be securely grasped on its projecting end 9b which simplifies making the needle cap from its components.

The distances over which the needle cap is drawn while the seal for the needle opening and the seal for connection of the injector head-needle cap are maintained are the maximum distances A, B shown in the figures.

The inner soft elastic lining member 6 is held like a cork in the opening 9. Furthermore the embodiment according to FIG. 3 has a constraining guide 10 for the injection needle 4 comprising a reinforced wall of the outer plastic casing 5, which simplifies the manipulations on insertion of the needle cap 1.

It is possible to sterilize the needle by a steam sterilization process after the cap has been put on the injector head in the embodiments with the open needle cap (FIGS. 2 and 3), since steam can be easily forced through the soft elastic part, i.e. the lining member 6. If an additional steam opening ventilation of the needle cap is necessary at the injector head, this can be guaranteed by a labyrinth seal. This labyrinth seal allows a passage of steam during the steam sterilization, however it provides a microbiological seal. The labyrinth seal is not shown in FIGS. 1 to 7.

Figure 4:
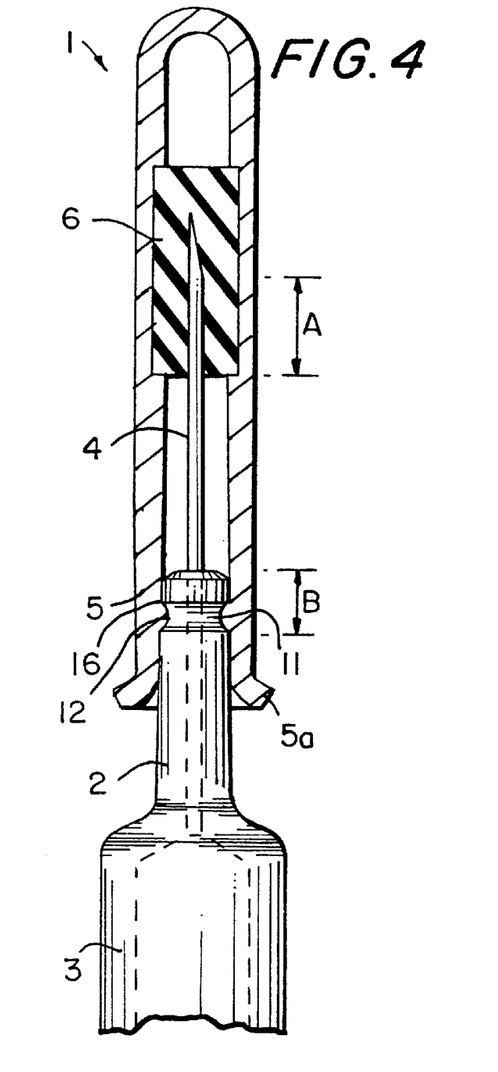
FIG. 4 is a cross-sectional view through a needle cap device according to the invention, according to FIG. 1, however with a snap connection between the cap and the needle body formed somewhat differently.

FIG. 4 shows an embodiment of the needle cap according to the invention similar to FIG. 1, however with another embodiment of a snap coupling or connection. This has been accomplished in the case of the embodiment according to FIG. 4 by providing a groove-like circumferential depression 11 in the injector head 2 and a complementary circular bulged portion 12 on the inner wall of the plastic casing 5. In other ways the form of the needle cap according to FIG. 4 corresponds to that of the other embodiments made up to now.

Figure 5:
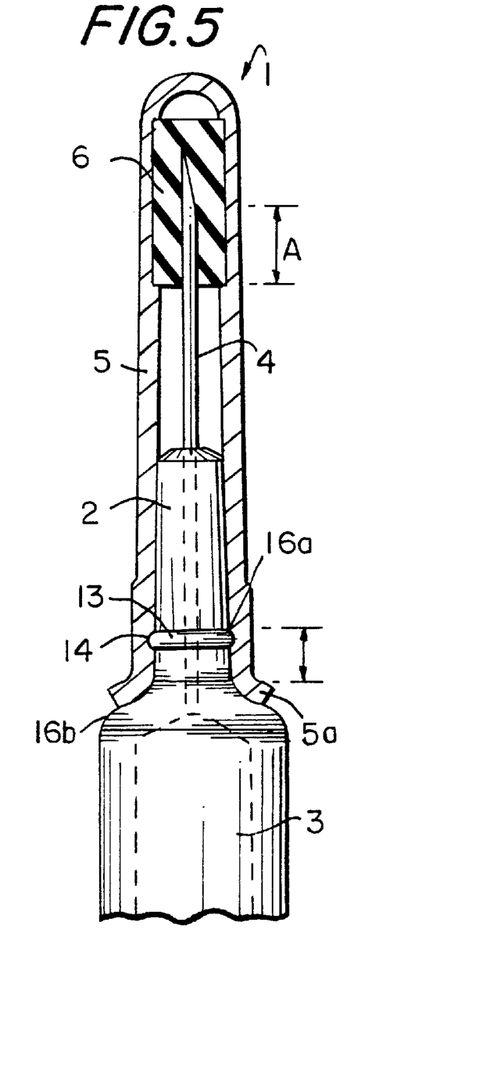
FIG. 5 is a cross-sectional view through another embodiment of a needle cap device according to the invention with an outer plastic casing, according to FIG. 1, however with a different snap connection and a conical injector head for constrained displacement-dependent ventilation of the cap interior.

FIG. 5 shows an embodiment of the needle cap according to the embodiment of FIG. 1 and similar to that of FIG. 4, in which a further variant of both the snap coupling and the displacement-dependent constrained aeration device are present. In the embodiment according to FIG. 5 the form-fitting connection in the form of the snap coupling is formed by a ring-like bulged portion 13 and a complementary recess 14 in the inner wall of the plastic casing 5. The plastic casing 5 has a somewhat thicker wall thickness in a lower region for increased mechanical stability. In contrast to the embodiments described heretofore, the injector head 2 is conical in form in the embodiment according to FIG. 5, tapering toward its tip so that a constrained aeration of the cap interior occurs by means of this conicity during removal of the needle cap. The stiffness of the plastic casing 5 prevents it from fitting the conicity of the injector head 2 in order to allow the displacement dependent constrained aeration. The stops 16a and 16b provide for controlled displacement during insertion processes.

Figures 6, 7:
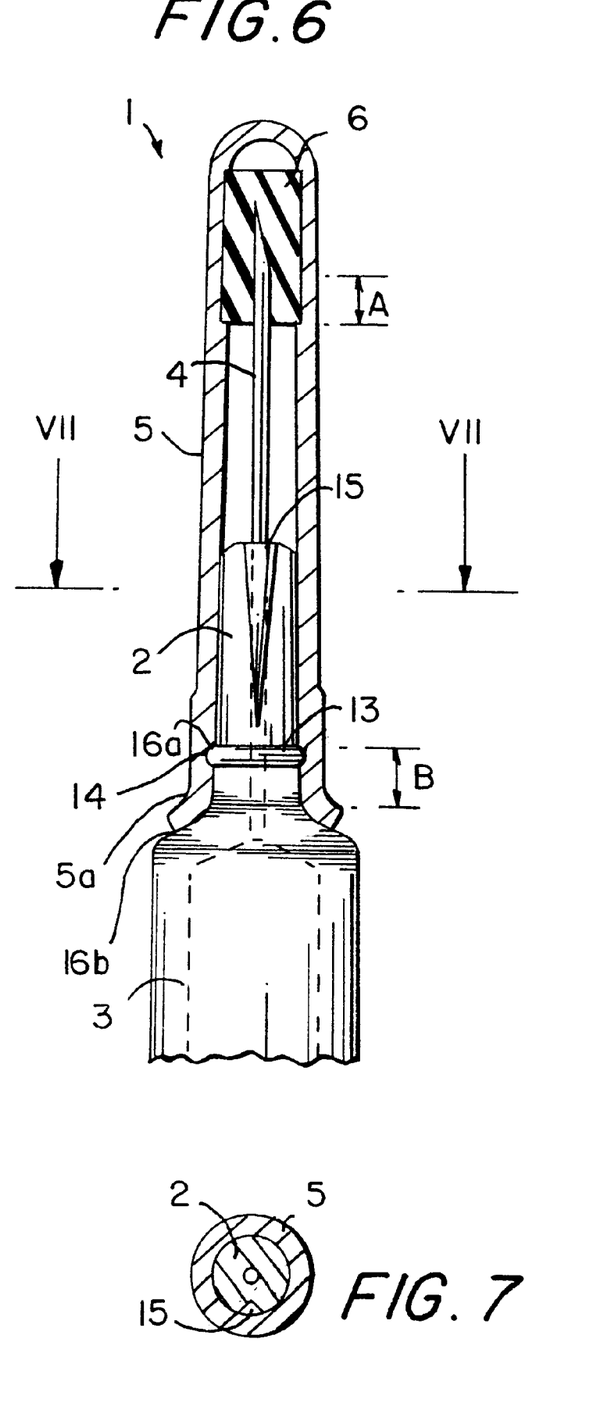
FIG. 6 is a cross-sectional view through an additional embodiment of a needle cap device, similar to that of FIG. 5, however with a V-groove in the injector head for constrained ventilation of the cap interior when the cap is pulled off the injector head.
FIG. 7 is a transverse cross-sectional view through the needle cap device according to FIG. 6 taken along the section line VII—VII shown there.

FIG. 6 shows an embodiment with the transverse cross-section according to FIG. 7 which is generally according to that of FIG. 5, with the difference that the injector head 2 has a V-shaped longitudinal groove 15 which widens toward and is open at its tip and the constrained aeration of the interior to the cap is effected progressively during removal of the cap 5 and thus allows a drop-free removal of the needle cap 1.

The disclosure in German Patent Application 197 17 033.1-35 of Apr. 23, 1997 is incorporated here by reference. This German Patent Application describes the invention described hereinabove and claimed in the claims appended hereininbelow and provides the basis for a claim of priority for the instant invention under 35 U.S.C. 119.

While the invention has been illustrated and described as embodied in a needle cap for a pre-fillable one-time injection apparatus, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A needle cap device for a pre-fillable single-use hypodermic syringe device, said single-use hypodermic syringe device comprising an injector head (2) and an injector needle (4) extending from the injector head and having a tip, wherein said needle cap device includes a stiff plastic outer casing (5) made of a hard elastic material that is sufficiently transparent so that the injector needle is visible when the outer casing (5) is connected to the injector head (2);

a sealing lining member (6) made of a soft material and arranged inside the stiff plastic outer casing (5), said sealing lining member having a predetermined shape to fit in the stiff plastic outer casing so that the tip of the injector needle (4) is inserted in the sealing lining member (6) when the outer casing (5) is connected to the injector head (2); and means (7,8; 11,12; 13,14) for connecting the stiff plastic outer casing (5) with the injector head (2) so that said outer casing (5) directly contacts said injector head (2) to provide a microbiological seal of an interior of the outer casing from an exterior thereto and to provide a stable mechanical connection of the injector head to the outer casing that limits displacement of the outer casing on the injector head when the injector head is inserted in the outer casing;

wherein the means for connecting, the lining member, the outer casing and the injector head are positioned and dimensioned so that an opening in the tip of the injector needle is not released from the sealing lining member (6) of the outer casing (5) until a pressure in the interior of the outer casing corresponds to an external air pressure during removal of the outer casing from the injector head (2), whereby a drop-free removal of the sealing lining member from the injector needle occurs.

2. The needle cap device as defined in claim 1, wherein said means for connecting is a snap coupling.

3. The needle cap device as defined in claim 2, wherein the means for connecting includes a groove-like circumferential depression (11) provided around said injector head (2) and a complementary bulged portion (12) provided on an interior wall of the outer casing (5).

4. The needle cap device as defined in claim 2, wherein the means for connecting comprises a circular bulged portion or a circular thickened portion (7,13) on the injector head (2) and a complementary recess (8,14) fitting said bulged or thickened portion.

5. The needle cap device as defined in claim 1, wherein the injector head (2) tapers conically to a tip of the injector head to facilitate aeration of the interior of the outer casing (5).

6. The needle cap device as defined in claim 1, wherein the injector head (2) has a longitudinal groove (15) for aeration of the interior of said outer casing (5).

7. The needle cap device as defined in claim 6, wherein the longitudinal groove (15) is V-shaped and widens in the direction of a tip of the injector head (2).

8. The needle cap device as defined in claim 1, wherein the means for connection has an axial position and the lining member (6) has an axial extent adjusted to each other such that, before the tip of the injector needle is released from the lining member (6) during removal of the needle cap, the interior of the outer casing (5) is aerated.

9. The needle cap device as defined in claim 1, wherein the stiff plastic outer casing (5) is closed on all sides.

10. The needle cap device as defined in claim 1, wherein the stiff plastic outer casing (5) has a casing tip and is provided with an opening at the casing tip and the comparatively soft lining member (6) is inserted in the opening in the casing tip to provide a microbiological seal of the opening in the casing tip.

11. The needle cap device as defined in claim 1, wherein the stiff plastic outer casing (5) has a constraining guide (10) for the injector needle (4) in the interior thereof.

12. A pre-fillable single-use hypodermic syringe device comprising a hollow injector body (3) provided with an injector head (2);

an injector needle (4) connected to the injector head (2) and having an opening in the vicinity of a tip of the injector needle; and     a needle cap device (1) comprising a stiff plastic outer casing (5) made of a hard elastic material and a sealing lining member (6) made from a soft material and fitting inside the stiff plastic outer casing (5) so that, when the outer casing (5) is mounted on the injector head (2), the injector needle (4) is closed by the sealing lining member (6); and     means for connecting the injector head with the stiff plastic outer casing (5) of the needle cap device so that said outer casing (5) directly contacts said injector head (2) to provide a mechanically stable connection of the injector head with the outer casing limiting displacement of the outer casing (5) on the injector head (2) and to provide a microbiological seal of an interior of the outer casing (5) from an exterior thereto, said means for connecting including elements (7,8; 11,12; 13,14) provided on the injector head (2) and the stiff plastic outer casing (5);

wherein the stiff plastic outer casing (5) of the needle cap device is made of a transparent or semitransparent translucent plastic material so that the injector needle is visible even when the outer casing (5) is connected to the injector head (2), said means for connecting has only one stop position and the means for connecting, the injector head (2), the lining member (6) and the outer casing (5) are dimensioned and positioned so that the opening of the tip of the injector needle is not released from the lining member of the outer casing on removal of the outer casing (5) until a pressure in an interior of the outer casing corresponds to an external air pressure, whereby a drop-free removal of the sealing lining member from the injector needle occurs.

\* \* \* \* \*

UNITED STATES PATENT AND TRADEMARK OFFICE
CERTIFICATE OF CORRECTION

PATENT NO. : 5,980,495
DATED : November 9, 1999
INVENTOR(S) : Heinz, J. et. al.

It is certified that error appears in the above-identified patent and that said Letters Patent is hereby corrected as shown below:

Title page, item [73], Assignee: delete -- Class KGaA, Harsewinkel, Germany-- and substitute "Schott Glas, Mainz, Germany"--

Signed and Sealed this

Twelfth Day of September, 2000

*Attest:*

Q. TODD DICKINSON

*Attesting Officer*       *Director of Patents and Trademarks*